United States Patent [19]

Martino et al.

[11] Patent Number: 5,030,388

[45] Date of Patent: Jul. 9, 1991

[54] EMULSIFIABLE TRIGLYCERIDE COMPOSITIONS

[75] Inventors: Gary T. Martino, Dayton; Martin M. Tessler, Edison, both of N.J.

[73] Assignee: National Starch and Chemical Investment Holding Corporation, Wilmington, Del.

[21] Appl. No.: 437,953

[22] Filed: Nov. 17, 1989

Related U.S. Application Data

[62] Division of Ser. No. 742,664, Jun. 7, 1985.

[51] Int. Cl.$^5$ .................................................. C11C 3/02
[52] U.S. Cl. .............................. 260/410.7; 260/410.6
[58] Field of Search ........................... 260/410.7, 410.6

[56] References Cited

U.S. PATENT DOCUMENTS

| | | | |
|---|---|---|---|
| 2,188,882 | 1/1940 | Clocker | 260/405 |
| 2,188,884 | 1/1940 | Clocker | 91/66 |
| 2,188,887 | 1/1940 | Clocker | 134/24 |
| 2,188,888 | 1/1940 | Clocker | 260/405 |
| 2,275,843 | 3/1942 | Clocker | 260/22 |
| 3,066,159 | 11/1962 | DeGroote et al. | 260/404 |
| 3,253,938 | 5/1966 | Hunt | 106/252 |
| 3,433,754 | 3/1969 | Honel | 260/22 |
| 3,968,310 | 7/1976 | Stowell | 428/411 |
| 4,075,145 | 2/1978 | Russell | 260/22 |

FOREIGN PATENT DOCUMENTS

| | | | |
|---|---|---|---|
| 60-99074 | 6/1985 | Japan . | |
| 0785474 | 10/1975 | United Kingdom | 260/410.7 |

*Primary Examiner*—Jose G. Dees
*Assistant Examiner*—Deborah D. Carr
*Attorney, Agent, or Firm*—Edwin M. Szala; Lori D. Tolly

[57] ABSTRACT

Water dispersible, self-emulsifiable triglyceride compositions are provided. The compositions comprise the reaction product of a) a triglyceride oil/olefinic acid (or anhydride) addition product and b) a water soluble monofunctional polyalkylene oxide.

13 Claims, 1 Drawing Sheet

EMULSIFIABLE TRIGLYCERIDE COMPOSITIONS

This application is a division of application Ser. No. 742,664, filed June 7, 1985.

BACKGROUND OF THE INVENTION

This invention relates to novel water dispersible, self-emulsifiable triglyceride compositions.

Condensation products of conjugated and nonconjugated unsaturated fatty esters or acids with acyclic olefinic acids or acid anhydrides have been prepared. Due to the acid or acid anhydride reactive site present on the condensation products, they have been employed as intermediates in the preparation of many different products having various useful properties.

For example, U.S. Pat. Nos. 2,188,882; 2,188,884; 2,188,887 and 2,188,888 (all issued Jan. 30, 1940 to E. Clocker) are directed to the condensation products of nonconguated, unsaturated, nonhydroxylated aliphatic acids, salts and esters thereof having 10-24 carbon atoms (including glyceryl esters which form oils) with acyclic olefinic acids or anhydrides such as maleic anhydride. It is taught that the condensation products may be further reacted with oxides, hydroxides, carbonates, and acetates in order to produce driers useful, for example, in the paint industry. It is also taught that the condensation products may be esterified with various aliphatic or aromatic mono- and poly-hydric alcohols. Some esterified products exhibit air drying and thermohardening properties useful in the paint and coating industry. Other esterified products are useful as dispersing and bodying agents in polish and cosmetic applications. The water-soluble salts of the esterified products are taught to be useful in the emulsification of oily materials such as fats, oils and waxes. U.S. Pat. No. 2,275,843 (issued Mar. 10, 1942 to E. Clocker) teaches that polyhydric alcohols (i.e., ethylene glycol) and poly-hydric alcohols containing ether groups (i.e., ethylene glycol monoethyl ether) are useful as etherifying agents for the condensation products in the preparation of resinous compounds.

U.K. Pub. No. 785,474 (published Oct. 30, 1957 to Boehme Fetichemic Gmbh.) is directed to water soluble dispersing and emulsifying agents prepared by reacting a polybasic carboxylic acid or ester containing at least one lipophilic group (i.e., unsaturated fatty acid or ester reacted with maleic anhydride) with polyalkylene oxides including polyethylene glycol.

U.S. Pat. No. 3,433,754 (issued Mar. 18, 1969 to H. Honel) is directed to hardenable synthetic resins prepared by the polyesterification of maleated esters of unsaturated conjugated or nonconjugated fatty acids with diols (i.e., polyethylene glycol).

U.S. Pat. No. 4,075,145 (issued Feb. 21, 1978 to R. H. Russel) is directed to water soluble resins prepared by polyesterifying a maleated triglyceride oil with at least one dicarboxylic acid or anhydride and one or more polyols.

U.S. Pat. No. 3,253,938 (issued May 31, 1966 to T. Hunt) is directed to surface coating polyester resins prepared by esterifying the condensation product of a triglyceride ester of an unsaturated fatty acid and an olefinic carboxylic acid or anhydride. The esterifying reagents employed may be any mono- or poly-hydric alcohol containing at least one $\alpha,\beta$-ethylenically unsaturated ether group (i.e., glycerol diallyl ether).

Epoxidized fatty acid derivatives (including triglyceride oils) have been reacted with oxyalkylation-susceptible poly-hydric alcohols and poly-hydric alcohols containing ether groups in order to provide ethers possessing surface active properties. See, for example, U.S. Pat. No. 3,066,159 (issued Nov. 27, 1962 to M. De Groote et al.).

None of the above references contemplate or disclose the novel compositions of the present invention.

SUMMARY

A water dispersible, self-emulsifiable triglyceride composition is provided which comprises the reaction product of:
a. an addition product of a triglyceride oil of an unsaturated fatty acid having at least 12 carbon atoms in the fatty acid chain and an olefin selected from the group consisting of acyclic olefinic carboxylic acids and the acid anhydrides thereof having less than 10 carbon atoms in their carbon chain and wherein the double bond of the olefin is $\alpha,\beta$-to the carboxylic acid group; and
b. a water soluble compound selected from the group consisting of a monohydroxy- or monoamino-terminated blocked polyalkylene oxide and mixtures thereof;

wherein the reaction product so produced is water dispersible and self-emulsifiable.

DESCRIPTION OF THE PREFERRED EMBODIMENTS

By the term "triglyceride oil" is meant the triester of glycerol and the same or mixed fatty acids. Fatty acid refers to straight chain monocarboxylic acids having a carbon chain length of from $C_{12}$ to $C_{30}$. Typical triglyceride oils useful herein are the glycerol esters of both conjugated and unconjugated fatty acids including, for example, corn oil, soybean oil, sunflower oil, safflower oil, linseed oil, perilla oil, cotton seed oil, tung oil, peanut oil, oiticica oil, hempseed oil, marine oil (i.e., alkali-refined fish oil), and dehydrated castor oil. The use of long chain fatty acids are not encompassed in the present invention.

The acyclic olefinic carboxylic acids useful herein are those having less than 10 carbon atoms in the carbon chain and the acid anhydrides thereof. The preferred acids are dicarboxylic-acids- including, for example, maleic acid, fumaric acid, citraconic acid, and itaconic acid. Those olefinic acids (and anhydrides) which are too stearically hindered at or near the point of unsaturation and, as such, are not useful herein (i.e., dimethyl-maleic anhydride) may be easily determined by one skilled in the art. Maleic acid is the preferred acyclic, olefinic carboxylic acid and it is preferably employed in the form of maleic anhydride which is relatively inexpensive and readily available.

The conditions for the addition reaction of the triglyceride oil and the olefinic acid are known and the reaction product for use as the intermediate in the process of the present invention may be prepared by these known procedures. The starting mixture preferably incorporates a stoichiometric amount of olefinic acid with respect to the three unsaturated fatty acid chains present in the triglyceride oil to be reacted. In other words, for each molecular equivalent of triglyceride oil to be reacted, we employ three molecular equivalents of olefinic acid. More or less olefinic acid may be employed, however, if desired.

The reaction is usually effected by heating the reactants together in an inert atmosphere (i.e., in a nitrogen stream) for an extended period of time at temperatures commonly below 300° C. until substantially all of the olefinic acid is chemically combined with the fatty acid chains of the oil. Temperatures of at least 110° C. should be employed if triglycerides of conjugated fatty acids are to be reacted while temperatures of at least 200° C. must be employed with triglycerides of unconjugated fatty acids. Herein, corn oil is preferably reacted with maleic anhydride, for example, at temperatures between 200° and 260° C. The reaction can be effected in the presence or absence of a catalyst. Suitable examples of catalysts which can optionally be used in the reaction are strong acids such as sulfuric acid, hydrochloric acid and the like, sulfonic acids such as toluenesulfonic acid and the like, sulfonic acid-type cation exchange resins, Friedel-Crafts catalysts such as aluminum chloride, and the like. Although the reaction time depends upon the types of reactants and conditions employed, the reaction usually is completed within about 2 to 10 hours after the predetermined temperature is reached.

When employing maleyl compounds (i.e., maleic anhydride), no catalyst is needed as the compounds easily undergo reactions with double bonds. Maleic anhydride may form ring adducts with conjugated fatty acid triglycerides via the Diels-Alder reaction. Also maleic anhydride reacts by addition with single double bonds resulting in a branch on the fatty acid group attached by a single carbon-carbon bond.

For the purposes of the present invention, it is necessary in the initial reaction of the triglyceride oil with the olefinic acid or anhydride to avoid mere esterification of alcohol groups, as distinguished from addition at the double bond of the oil. Due to the difficulty in achieving addition between the olefinic acid or anhydride and the triglyceride oil herein, due to the change in properties caused by esterification (i.e., gelling), only nonhydroxylated oils or those not sufficiently hydroxylated to interfere with the addition reaction are recommended for use herein.

The reactants should be reasonably dry and water formed by decomposition during the reaction should be removed in order to prevent or minimize hydrolysis. For example, if maleic acid is to be reacted with the triglyceride oil, it is preferable to use a relatively high temperature to cause a rapid reaction. It is also preferable to allow elimination of any water formed by decomposition of the maleic acid into maleic anhydride by, for example, avoiding refluxing and permitting distillation. Conversely, when maleic anhydride is employed, the reaction is carried out under reflux conditions in order to return to the mixture any maleic anhydride which boils or sublimes off.

The novel water dispersible, self-emulsifiable compounds of the present invention are prepared by the esterification or amidification of the triglyceride oil-/olefinic-acid (or anhydride) addition product described above by a blocked polyalkylene oxide compound which contains only one reactive (i.e., hydroxyl or amino) group capable of reacting with the acid or anhydride moiety of the triglyceride product. The polyalkylene oxide units, which may be the same or a mixture of different alkylene oxides, comprise alkylene units of 2 to 5, preferably 2 to 3, carbon atoms. Particularly useful herein are water soluble polyoxyethylene compounds having molecular weights of about 300 to 2700 which are often utilized as nonionic surfactants.

The number of ethylene oxide units can range from about 7 to about 60, preferably 8 to 17. Use of polyhydroxy or polyamino compounds which result in crosslinked products that do not exhibit water-dispersibility and self-emulsifiability are not suitable herein.

The blocked polyalkylene oxide compounds may be terminated with small alkyl or alkenyl groups in the $C_1$ to $C_4$ range. Longer end blocking groups such as $C_8$ to $C_{18}$ alkyl, aryl, and aralkyl groups may also be employed as long as the polyalkylene oxide portion of the compound has sufficiently higher hydrophilicity to balance the hydrophobicity of the end blocking group, as well as the triglyceride product to be reacted. It is understood that the end blocking groups are residues of the polyalkylene oxide compound and an active hydrogen atom containing compound capable of reaction with alkylene oxides including, for example, phenols, alcohols, amines, mercaptans, and carboxylic acids.

Less than an equimolar amount of the blocked polyalkylene oxide may often be reacted with the triglyceride oil addition product in order to produce the water dispersible, self-emulsifiable products. The minimum amount necessary will vary depending, for example, on the molecular weight and hydrophilic character of the polyalkylene oxide employed. It should be understood that larger than equimolar quantities of the polyalkylene oxide may be employed in some cases, however, such amounts are not necessary for the purposes herein. Stearic interference between the fatty acid chains of the oil and more than one polyalkylene oxide substituent may hinder the feasibility of employing greater than equimolar amounts of the polyalkylene oxide. It should also be recognized that when greater than equimolar amounts are employed, the ester or amide reaction product may be rendered too hydrophilic (i.e., water soluble) and as such, would not be suitable herein. Therefore, the esterification or amidification reaction preferably employs one mole of the triglyceride oil addition product and 0.1 to 1.0 moles of the polyalkylene oxide.

The esterification or amidification reaction may be conducted in the presence of the triglyceride oil addition product and the blocked polyalkylene oxide as the sole reaction media ingredients. The compounds herein may be prepared under relatively mild conditions by merely heating the reactants for several hours at temperatures above the melting point of the polyalkylene oxide reactant (typically 30 to 80° C.). Suitable reaction temperatures will range from about 50° to 190° C., preferably 90° to 120° C. Although not necessary, the reaction is preferably conducted in the presence of an inert gas (i.e., nitrogen).

Suitable organic solvents and/or catalysts may be employed, if desired, as long as they do not adversely affect the reaction. While various catalysts are known in the art to be useful in the esterification reaction, we preferably employ trialkylamines (i.e., triethylamine) in amounts of about 0.1 to 2.0% (preferably 0.5%) based on the weight of the triglyceride oil reactant to catalyze the reaction.

Due to the self-emulsifying properties possessed by the compositions of the present invention, they may find utility as emulsifying agents for various compounds useful in aqueous emulsion form such as, for example, cellulose reactive sizing agents. Typical sizing agents include hydrocarbyl-substituted cyclic dicarboxylic acid anhydrides which are described in U.S. Pat. Nos. 3,102,064 (issued to Wurzburg et al. on Aug. 27, 1963), 3,821,069 (issued to Wurzburg on June 28, 1974), and 4,040,900 (Re. 29,960 reissued to E. Mazzarella on Apr. 10, 1979).

The following examples are merely illustrative and should not be construed as limiting the scope of the invention. In the examples, all parts and percentages are given by weight and all temperatures are in degrees Celsius.

The emulsifiability of the products exemplified herein was determined by the following laboratory test:

DISPERSIBILITY TEST

To a 10 ml. beaker containing 5 ml. water is added 0.5 g. of test product. The mixture is then agitated with a magnetic stirring bar for 30 minutes. After stirring is discontinued, the mixture is allowed to stand for 30 minutes prior to characterization. Visual observations were recorded for each sample according to the following rating scale:

| Rating | Appearance Upon Standing for 30 Minutes |
| --- | --- |
| Soluble | Completely water soluble. |
| Good | Dispersion is translucent to opaque, Homogeneous (no phase separation). |
| Poor | Non-homogeneous with all or a portion of sample being undispersed. |

EXAMPLE 1

This example illustrates the addition reaction of a triglyceride oil with a dicarboxylic acid anhydride useful herein. Specifically, corn oil was reacted with sufficient maleic anhydride (MA) in order to maleate approximately all three fatty acid chains of the triglyceride.

To a 250 ml. round bottom flask equipped with a thermometer, reflux condensor, and agitator was added 100 g. corn oil (MW≈884) and 35 g. maleic anhydride (MW=98). The mixture was heated under nitrogen purge to 200° C. and allowed to react for 1 hour. Thereafter, the temperature was raised to 230° C. The reaction was continued until the free maleic anhydride peak due to vinyl hydrogen (841 cm$^{-1}$) vanished as followed by Infrared Spectroscopy. The 3.2:1 molar maleic anhydride: corn oil addition product (MACO) was recovered in approximately 99% yield.

EXAMPLE 2

This example illustrates the preparation of other addition products which are useful as intermediates herein.

The triglyceride oils listed below were successfully reacted with 35% of maleic anhydride as in Example 1:
Safflower oil
Soybean oil
Sunflower oil.

Samples of corn oil were also reacted as described in Example 1 with 30–35% of the following anhydrides:
citraconic anhydride
itaconic anhydride
bromomaleic anhydride
dichloromaleic anhydride
2,3-dimethylmaleic anhydride
cis-1,2,3,6-tetrahydrophthalic anhydride.

The first four anhydride reagents readily reacted with the oil to yield the desired addition products. The addition reaction employing the 2,3-dimethylmaleic anhydride was unsuccessful due to what was believed to be stearic interference. As such, this olefinic reagent is not suggested for use herein. The addition reaction employing the tetrahydrophthalic anhydride was also unsuccessful, showing the olefinic acids (and anhydrides thereof) which are useful herein must have the double bond $\alpha,\beta$- to the carboxylic acid or anhydride group and must not be stearically hindered.

EXAMPLE 3

This example illustrates the esterification reaction of the maleated corn oil of Example 1 with a monohydroxy terminated blocked polyalkylene oxide.

To a similar apparatus as described in Example 1, 100 g. of 3.2:1 MACO was charged with 30 g. polyethylene glycol monomethyl ether (PEGMME) 350. The 1:1 molar PEGMME 350: MACO mixture was heated under nitrogen purge to 115° C. Thereafter, 0.5 g. triethylamine catalyst was added. The reaction was continued until the decrease of the carbonyl peak of the cyclic anhydride (1780 cm$^{-1}$) stabilized as followed by Infrared Spectroscopy. The product was recovered in approximately 99% yield. When evaluated by the Dispersibilty Test, a good emulsion was observed. See Table I for results.

EXAMPLE 4

This example demonstrates the inferior emulsifiability of an esterified maleated fatty acid and fatty ester in comparison to the esterified maleated triglyceride oil of the present invention.

One hundred gram samples of oleic acid and ethyl oleate were reacted with maleic anhydride (35 g and 31.6 g, respectively) as described in Example 1 in order to provide each molecule of the fatty acid or ester with one maleic anhydride group. Thereafter, the addition products were reacted with an equimolar amount of PEGMME 350 according to the procedure of Example 3.

The esterified products were compared for dispersibility with the esterified triglyceride product of Example 1. The results may be found in Table I.

TABLE I

| Addition Product | Molar Ratio of PEGMME 350: Addition Product | Dispersibility Test Observations |
| --- | --- | --- |
| 1:1 Molar MA:Oleic Acid | 1:1 | Poor |
| 1:1 Molar MA:Ethyl Oleate | 1:1 | Soluble |
| 3.2:1 Molar MACO | 1:1 | Good |

The results show that various fatty acid compounds which are maleated with equivalent amounts of maleic anhydride, based on the degree of unsaturation of the compound, do not exhibit the emulsifiability properties of similarly treated triglyceride fatty acids when esterified with equimolar amounts of a monohydroxy-terminated blocked polyalkylene oxide found useful herein.

EXAMPLE 5

This example illustrates the preparation of other water-dispersible, self-emulsifiable products of the present invention.

Samples of the corn oil addition products of Examples 1 and 2 were esterified with 30% PEGMME 750 according to the procedure of Example 3. The reaction data and dispersibility test results of the products may be found in Table II.

TABLE II

| Olefin:Corn Oil Addition Product | | Molar Ratio of PEGMME 750: Addition Product | Dispersibility Test Observations |
|---|---|---|---|
| Molar Ratio | Olefin | | |
| 3.2:1 | maleic anhydride | 0.5:1 | Good |
| 2.4:1 | citraconic anhydride | 0.5:1 | Good |
| 2.4:1 | itaconic anhydride | 0.5:1 | Good |
| 1.5:1 | bromomaleic anhydride | 0.5:1 | Good |
| 1.6:1 | dichloromaleic anhydride | 0.5:1 | Good |

EXAMPLE 6

This example illustrates the effect of the molecular weight of the hydrophilic reagents useful herein.

A series of water soluble, monohydroxy-terminated blocked monoand polyalkylene oxides were reacted with MACO and evaluated for dispersibility. The products were reacted according to the procedure of Example 3. The reaction data and dispersibility test results may be found in Table III.

TABLE III

| MACO Molar Ratio | Ethylene Glycol Reagent (MW) | Molar Ratio Reagent:MACO | Dispersibility Test Observations |
|---|---|---|---|
| 3.2:1 | methoxyethanol (76) | 2.4:1 | Poor |
| 5.4:1 | methoxyethanol (76) | 5.7:1 | Poor |
| 3.2:1 | diethylene glycol MME (120) | 2:1 | Poor |
| 2.3:1 | 2-(2-methoxyethoxy)ethanol (162) | 1.4:1 | Poor |
| 3.2:1 | 2-(2-methoxyethoxy)ethanol (162) | 1.5:1 | Poor |
| 3.2:1 | tripropylene glycol MME (206) | 3.2:1 | Poor |
| 3.2:1 | PEGMME (350) | 0.7:1 | Poor |
| 3.2:1 | PEGMME (350) | 1:1 | Good |
| 2.3:1 | PEGMME (750) | 0.4:1 | Good |
| 3.2:1 | PEGMME (750) | 0.2:1 | Poor |
| 3.2:1 | PEGMME (750) | 0.5:1 | Good |
| 3.2:1 | PEGMME (750) | 1:1 | Soluble |
| 4.1:1 | PEGMME (750) | 0.5:1 | Good |
| 3.2:1 | PEGMME (5000) | 0.05:1* | Poor |

*The product was a waxy solid.

As can be seen by the results, the polyalkylene oxides useful herein are those having molecular weights greater than about 300. In terms of repeating ethylene oxide units, only compounds having 7 or more repeating units provide products which are both water dispersible and self-emulsifiable. It is also shown that polyalkylene oxides which are too high in molecular weight, such as PEGMME 5000 (having approximately 113 ethylene oxide repeating units), are also not useful herein.

The series of 3.2:1 MACO samples which were reacted with 0.2-1 molar equivalents of PEGMME 350 or PEGMME 750 also showed that the amount of polyalkylene oxide reactant necessary to provide water dispersible, self-emulsifiable products will vary depending on the molecular weight of the reactant. For example, a smaller molar amount of PEGMME 750 compared to PEGMME 350 is necessary to provide an acceptable product. It is also seen that if an insufficient amount of polyalkylene oxide reactant is employed, the resultant product will provide poor dispersibility. Conversely, if too much of the reactant is employed, water soluble products may be produced.

EXAMPLE 7

This example illustrates the necessity of the polyalkylene oxides useful herein to be monofunctional.

Samples of MACO were reacted with polyethylene glycol (PEG) 300 and PEG 600 according to the procedure of Example 3. The esterified products were compared for dispersibility with similar samples of MACO which had been esterified with comparable PEGMME 350 and PEGMME 550. The reaction data and dispersibility test results may be found in Table IV.

TABLE IV

| MACO Molar Ratio | Molar Ratio of Polyalkylene Oxide Reactant:MACO | Dispersibility Test Observations |
|---|---|---|
| 3.2:1 | 0.8 PEG 300:1 | Poor |
| 3.2:1 | 1.25 PEG 300:1 | Poor |
| 3.2:1 | 1.0 PEGMME 350:1 | Good |
| 2.3:1 | 0.2 PEG 600:1 | Poor |
| 2.3:1 | 0.4 PEG 600:1 | Poor |
| 2.3:1 | 0.4 PEGMME 550:1 | Good |

The results show that the triglyceride addition products esterified with polyfunctional polyalkylene oxide reactants do not result in water dispersible, self-emulsifiable products. Less than or equivalent molar amounts of similar monofunctional reactants, however, did provide acceptable esterified products.

EXAMPLE 8

The hydrophobic character of the end-blocking groups of the polyalkylene oxides will effect the dispersibility of the products prepared herein as illustrated by the following example.

Samples of 2.3:1 and 3.2:1 MACO were reacted with various monohydroxy-terminated end-blocked polyethylene glycols according to the procedure of Example 3. Thereafter, the esterified products were compared for dispersibility. The reaction data and dispersibility results may be found in Table V.

TABLE V

| MACO Molar Ratio | Glycol Reactant End Blocking Group | EO* Units | Molar Ratio of Glycol Reactant: MACO | Dispersibility Test Observations |
|---|---|---|---|---|
| 3.2:1 | lauryl ether | 4** | 1.5:1 | Poor |
| 3.2:1 | lauryl ether | 23 | 0.4:1 | Good |
| 3.2:1 | octylphenyl ether | 10 | 0.8:1 | Poor |
| 3.2:1 | octylphenyl ether | 40 | 0.3:1 | Good |
| 2.3:1 | nonylpheyl ether | 9.5 | 0.6:1 | Good |
| 2.3:1 | nonylphenyl ether | 30 | 0.3:1 | Good |
| 3.2:1 | palmityl ether | 20 | 0.5:1 | Good |
| 3.2:1 | stearyl ether | 20 | 0.5:1 | Good |
| 3.2:1 | oleyl ether | 20 | 0.5:1 | Good |

*Ethylene Oxide **Reactant was not water soluble
**Reactant was not water soluble It is seen that the end blocking group of octylphenyl ether provided too much hydrophobic character to a reactant containing only 10 ethylene oxide (EO) repeating units, but was not too hydrophobic for use herein when attached to a similar reactant which contained 40 repeating units. The results show that polyalkylene oxide reactants containing hydrophobic end blocking groups are useful herein as long as the number of alkylene oxide repeating units of the reactant is large enough to provide sufficient hydrophilicity to balance the block group and triglyceride addition product.

EXAMPLE 9

This example illustrates other compositions encompassed herein prepared by the amidification of a triglyceride oil addition product with mono-amino blocked polyalkylene oxide compounds.

The amidification products were prepared by reacting 3.2:1 MACO with 30% of various amino-terminated hydrophilic polymers of the Jeffamine Series (registered trademark of Texaco). The polymers have the general formula

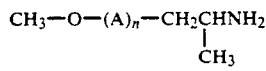

where A is ethylene oxide (EO), propylene oxide (PO), or a mixture thereof. The reaction data and dispersibility results may be found in Table VI.

TABLE VI

| MACO Molar Ratio | Amino-terminated Polymer PO/EO Ratio | MW | Molar Ratio of Polymer:MACO | Dispersibility Test Observation |
|---|---|---|---|---|
| 3.2:1 | 9/0 | 600 | 0.6:1 | Poor |
| 3.2:1 | 3/18 | 1000 | 0.4:1 | Good |
| 3.2:1 | 10/31 | 2070 | 0.2:1 | Good |

EXAMPLE 10

This example illustrates the usefulness of the compositions herein as emulsifiers for cellulosic sizing agents in a paper application. In order to obtain good sizing from a sizing agent, it is desirable that the agent be uniformly dispersed throughout the cellulosic fiber slurry in the form of an aqueous emulsion in as small a particle size possible.

Aqueous sizing emulsions were prepared employing:
(a) 0.5% mixed substituted alkenyl succinic anhydrides wherein the alkenyl groups of the mixed anhydrides contained 15-20 carbon atoms (referred to hereinafter as ASA),
(b) 6-15% emulsifier based on ASA, and
(c) 1.0% dispersed beta-diethyl aminoethyl chloride hydrochloride ether of corn starch, whose preparation is described in Example I of U.S. Pat. No. 2,813,093 (issued to C. Caldwell et al. on Nov. 12, 1957).

In Comparative Emulsion I, a typical polyoxyalkylene alkyl aryl ether emulsifier (A) described in U.S. Re. 29,960 (previously cited) was employed.

Test Emulsions II-V employed emulsifiers of the present invention which are described in Table III of Example 6. Emulsifier B was 3.2:1 MACO which had been esterified with 0.5 moles of PEGMME 750. Emulsifier C was 4.1:1 MACO which had been similarly esterified.

Calculated amounts of the emulsions prepared above were added to aqueous slurries of bleached sulfate pulp having a C.S.T. (Canadian Standard Freeness) of 350 cc., a consistency of 0.5%, and a pH of about 7.7 so as to yield a concentration of ASA on dry fiber weight of 0.25%. In a variation of this procedure, 0.5% alum, based on dry fiber weight, was added to the pulp slurry to give a pH of 7.5 before addition of the sizing emulsions. Sheets were formed in accordance with TAPPI standards, dried on a rotary print drier (surface temperature approx. 90° C.) then cured for 1 hour at 105° C. and conditioned overnight at 22° C. and 50% relative humidity before testing. The basis weight of these sheets was 55 lbs./ream (24×36 inch-500 sheets).

The Hercules Size Performance Test (HST) was employed to compare the ink resistance of the sheets prepared. The test comprises applying an amount of acid ink (pH 1.5) to the upper paper surface. With the use of a photoelectric cell, the underside of the paper is monitored for reflectance. The time it takes for the ink to cause a decrease in reflectance from 100% to 80% is the paper's HST time. The ink hold-out time of the paper is a measure of the sizing performance of a given size. The longer the HST time, the better the size is.

Table VII presents the particle size and internal sizing data for the above-described emulsions.

TABLE VII

| | Emulsifier Based % on ASA | Average Particle Size of Emulsion (Microns) | % Alum Addition | HST (seconds) |
|---|---|---|---|---|
| Emulsion I (Comparative) | 6% A | <1 | 0 | 289 |
| | 6% A | <1 | 0.5 | 360 |
| Emulsion II | 6% B | <1 | 0 | 253 |
| | 6% B | <1 | 0.5 | 384 |
| Emulsion III | 10% B | <1 | 0 | 284 |
| | 10% B | <1 | 0.5 | 339 |
| Emulsion IV | 15% B | <1 | 0 | 161 |
| | 15% B | <1 | 0.5 | 301 |
| Emulsion V | 10% C | * | 0 | 251 |
| | 10% C | * | 0.5 | 362 |

*Not measured

The results show that self-emulifiable compositions of the present invention satisfactorily emulsified a typical cellulosic sizing agent as noted by the particle size of the emulsion produced as well as by the comparable sizing results obtained in comparison to the control.

As will be recognized by those skilled in the art, the present invention provides novel water dispersible, self-emulsifiable triglyceride compositions. Variations may be made in ingredients, proportions, and procedures as long as such variations are within the scope and spirit of the following claims.

We claim:

1. A water dispersible triglyceride composition consisting essentially of the reaction product of:
   (a) an addition product of a triglyceride oil of an unsaturated fatty acid having at least 12 carbon atoms in the fatty acid chain and an olefin selected from the group consisting of acyclic olefinic carboxylic acids and the acid anhydrides thereof having less than 10 carbon atoms in their carbon chains and wherein the double bond of the olefin is $\alpha,\beta$ to the carboxylic acid group and the triglyceride oil and the olefin are employed in a molar ratio of 1 to about 1.5 to 4.1; and
   (b) a water soluble monohydroxy terminated blocked polyalkylene oxide having a molecular weight of from about 300 to 2,700;
wherein the reaction product is dispersible and self-emulsifiable in water.

2. The triglyceride composition of claim 1, wherein the triglyceride oil is nonhydroxylated.

3. The triglyceride composition of claim 2, wherein the fatty acid chain contains 12 to 18 carbon atoms.

4. The triglyceride composition of claim 1, wherein the triglyceride oil is selected from the group consisting of corn oil, safflower oil, soybean oil, and sunflower oil.

5. The triglyceride composition of claim 1, wherein the olefin is an acyclic olefinic acid anhydride.

6. The triglyceride composition of claim 5, wherein the anhydride is selected from the group consisting of maleic anhydride, citraconic anhydride, itaconic anhydride, bromomaleic anhydride, and dichloromaleic anhydride.

7. The triglyceride composition of claim 4, wherein the polyalkylene oxide contains ethylene oxide units, propylene oxide units or a mixture thereof.

8. The triglyceride composition of claim 7, wherein the polyalkylene oxide is polyethylene oxide.

9. The triglyceride composition of claim 8, wherein the blocking group of the polyethylene oxide is a $C_1$ to $C_4$ alkyl or alkenyl group.

10. The triglyceride composition of claim 9, comprising the reaction product of 1 mole of (a) and about 1 mole of (b), wherein (a) is the addition product of 1 mole of corn oil and about 3.2 moles of maleic anhydride and (b) is polyethylene glycol monomethyl ether 350.

11. The triglyceride composition of claim 9, comprising the reaction product of 1 mole of (a) and about 0.4 to less than 1 mole of (b), wherein (a) is the addition product of 1 mole of corn oil and about 2.3 to 4.1 moles of maleic anhydride and (b) is a polyethylene glycol monomethylether having a molecular weight of about 550 to about 750.

12. The triglyceride composition of claim 8, wherein the blocking group of the polyethylene oxide is a $C_5$ to $C_{18}$ alkyl, aryl, or aralkyl group.

13. The triglyceride composition of claim 12 comprising the reaction product of 1 mole of (a) and about 0.3 to about 0.6 moles of (b), wherein (a) is the addition product of 1 mole of corn oil and about 2.3 to about 3.2 moles of maleic anhydride and the polyethylene oxide of (b) contains about 10 to 40 ethylene oxide units.

* * * * *